(12) United States Patent
Brusacà et al.

(10) Patent No.: US 8,172,594 B2
(45) Date of Patent: May 8, 2012

(54) LOW INSERTION FORCE MULTI-POLE CONNECTOR DEVICE

(75) Inventors: Marco Brusacà, Genoa (IT); Federico Cau, Genoa (IT)

(73) Assignee: Esaote S.p.A., Milan (IT)

( * ) Notice: Subject to any disclaimer, the term of this patent is extended or adjusted under 35 U.S.C. 154(b) by 0 days.

(21) Appl. No.: 12/547,531

(22) Filed: Aug. 26, 2009

(65) Prior Publication Data
US 2010/0055991 A1    Mar. 4, 2010

(30) Foreign Application Priority Data
Aug. 27, 2008    (IT) .............................. GE2008A0072

(51) Int. Cl.
*H01R 11/22*    (2006.01)
(52) U.S. Cl. ........................................ 439/267; 439/266
(58) Field of Classification Search .................. 439/267, 439/260, 268, 259, 269.1, 262
See application file for complete search history.

(56) References Cited

U.S. PATENT DOCUMENTS

| | | | | |
|---|---|---|---|---|
| 1,917,009 | A * | 7/1933 | Betts et al. ..................... | 439/262 |
| 3,644,873 | A * | 2/1972 | Dalton et al. ................. | 439/299 |
| 3,724,322 | A * | 4/1973 | Reed ............................ | 89/1.811 |
| 3,917,372 | A * | 11/1975 | Selinko .......................... | 439/298 |
| 3,966,290 | A * | 6/1976 | Little et al. ..................... | 439/74 |
| 4,128,288 | A * | 12/1978 | Zachry et al. ................. | 439/152 |
| 4,141,616 | A * | 2/1979 | Gottlieb ......................... | 439/263 |
| 4,211,458 | A | 7/1980 | Kent | |
| 4,220,382 | A * | 9/1980 | Ritchie et al. .................... | 439/61 |
| 4,261,631 | A * | 4/1981 | Guilcher et al. .............. | 439/260 |
| 4,300,810 | A | 11/1981 | Brown et al. | |
| 4,540,227 | A * | 9/1985 | Faraci .............................. | 439/64 |
| 4,592,608 | A * | 6/1986 | Ohtsuka et al. ............... | 439/140 |
| 4,713,014 | A * | 12/1987 | Conroy-Wass ................. | 439/67 |
| 4,734,049 | A * | 3/1988 | George et al. ................. | 439/259 |
| 4,843,477 | A * | 6/1989 | Mizutani et al. .............. | 348/837 |
| 5,000,694 | A * | 3/1991 | Komatsu ....................... | 439/260 |
| 5,049,091 | A * | 9/1991 | Tanaka .......................... | 439/500 |
| 5,111,360 | A * | 5/1992 | Baba ............................. | 361/727 |
| 5,203,021 | A * | 4/1993 | Repplinger et al. ........ | 455/575.9 |
| 5,205,753 | A * | 4/1993 | Butterfield et al. ........... | 439/157 |
| 5,517,387 | A * | 5/1996 | Smith ....................... | 361/679.32 |
| 5,617,866 | A * | 4/1997 | Marian, Jr. .................... | 600/459 |

(Continued)

OTHER PUBLICATIONS

European Search Report issued in the corresponding Application No. EP 09 16 8092 dated Jan. 8, 2010.

*Primary Examiner* — Neil Abrams
(74) *Attorney, Agent, or Firm* — Buchanan Ingersoll & Rooney PC

(57) ABSTRACT

A multi-pole connector has a first movable or plug-in connector member (30) with a plurality of electric contacts (131) supported by a terminal strip (31). The electric contacts are arranged in a pattern. The movable member (30) is designed to be mechanically and electrically coupled to a framework (1) which includes a second stationary, spring-biased connector member (5) which has at least one terminal strip (4, 4') with a plurality of electric contact terminals (104, 104') thereon, in the form of islands of material arranged in the same pattern. The movable member (30) is to be inserted into a fixed slide guide (103) and the connector member (5) is urged by springs (7) to bring terminal strips (4, 4') into an electrical connection position with movable member (30) and a rotatable shaft (106) with cam (306) is used to move the stationary member (5) away from such position, to thereby permit release of the movable member (30).

25 Claims, 10 Drawing Sheets

U.S. PATENT DOCUMENTS

| | | | | |
|---|---|---|---|---|
| 5,709,562 A * | 1/1998 | Kourimsky | ................... | 439/267 |
| 5,752,841 A * | 5/1998 | Hori | ............................. | 439/108 |
| 5,795,172 A * | 8/1998 | Shahriari et al. | .............. | 439/260 |
| 5,846,097 A * | 12/1998 | Marian, Jr. | .................... | 439/289 |
| 5,855,488 A * | 1/1999 | Heintz et al. | ................. | 439/310 |
| 5,919,058 A * | 7/1999 | Tashiro et al. | ................ | 439/374 |
| 5,967,808 A * | 10/1999 | Kubota | ........................ | 439/157 |
| 6,116,762 A * | 9/2000 | Kutlucinar | ................... | 362/500 |
| 6,126,469 A * | 10/2000 | Yamaguchi | .................. | 439/310 |
| 6,164,999 A | 12/2000 | McCutchan et al. | | |
| 6,238,229 B1 | 5/2001 | Watanabe | | |
| 6,418,027 B1 * | 7/2002 | Suzuki et al. | ................. | 361/729 |
| 6,698,937 B2 * | 3/2004 | Grimes et al. | ................. | 385/53 |
| 6,769,927 B2 * | 8/2004 | Brewer | ........................ | 439/328 |
| 6,817,885 B2 * | 11/2004 | Josquin et al. | ................ | 439/374 |
| 6,926,548 B2 * | 8/2005 | Reasoner et al. | ............. | 439/310 |
| 7,022,080 B2 * | 4/2006 | Marian, Jr. | .................... | 600/459 |
| 7,291,032 B1 * | 11/2007 | Carver et al. | ................. | 439/310 |
| 7,654,844 B1 * | 2/2010 | Wormsbecher et al. | ...... | 439/259 |
| 7,681,482 B1 * | 3/2010 | Kubinski et al. | ............. | 89/1.811 |
| 7,731,516 B2 * | 6/2010 | Puttinger et al. | ............. | 439/260 |

* cited by examiner

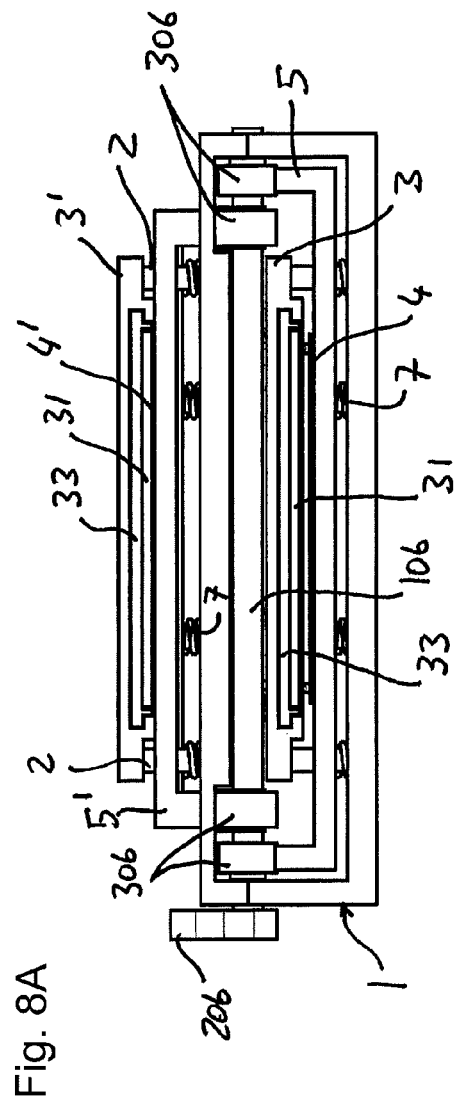
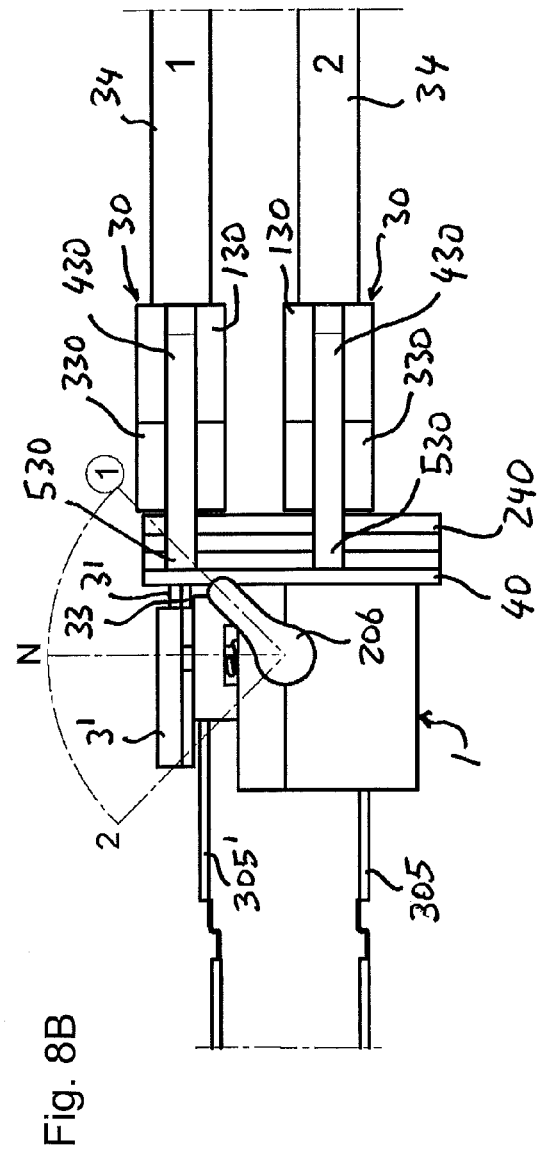
Fig. 8A
Fig. 8B

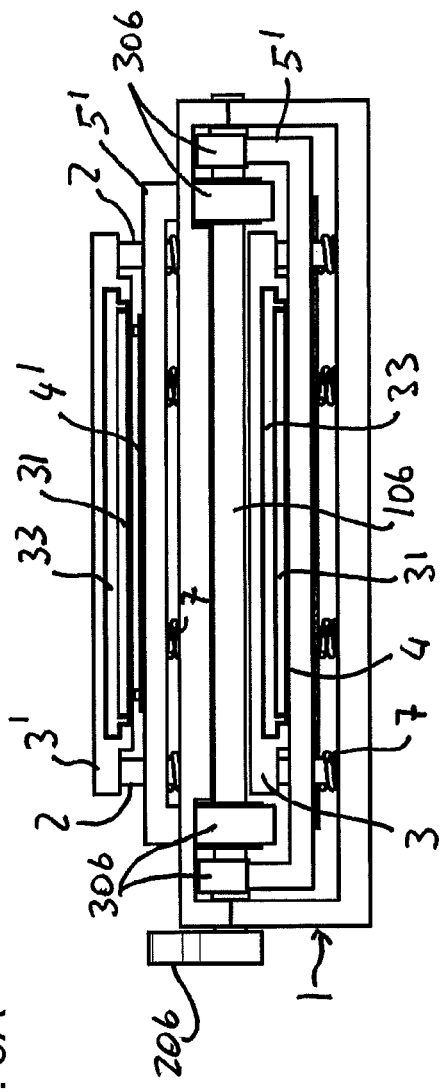
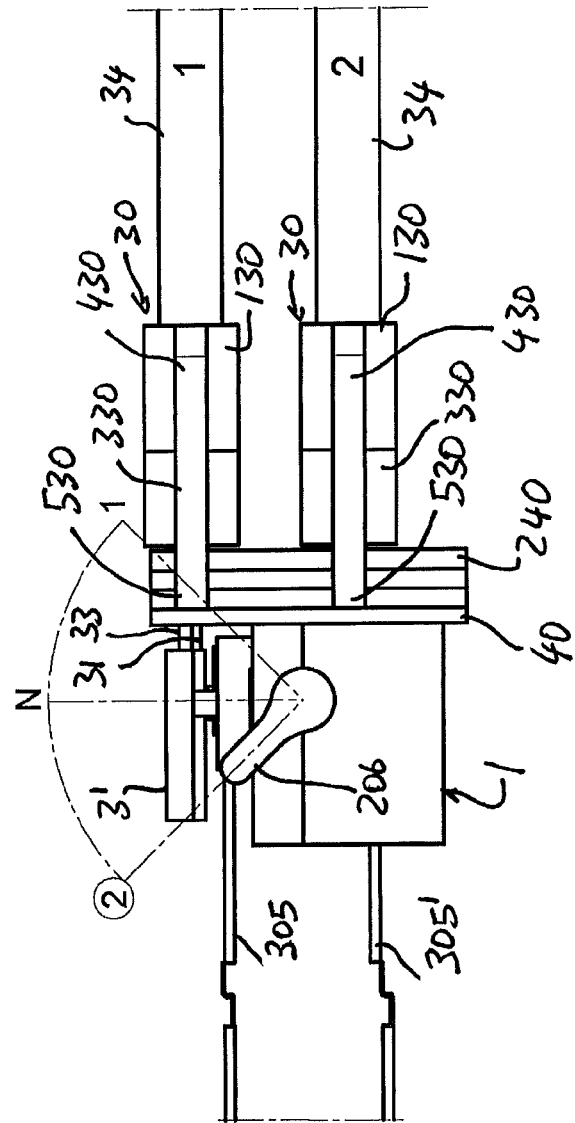
Fig. 9A
Fig. 9B though the connecting
LOW INSERTION FORCE MULTI-POLE CONNECTOR DEVICE The present invention relates to a multi-pole connector device, particularly a surface-to-surface Zero Insertion Force (ZIF) connector device for medical applications.

Connector devices of this type are used in the art of medical equipment for electric connection between the multi-pole cable of an ultrasound probe or the like and the circuits for controlling said probe and processing the signals collected by said probe.

Each signal acquired by each piezoelectric transducer of the transducer array of an ultrasonic probe is separately transferred to the medical apparatus, each along a separate line consisting of a dedicated wire, wherefore the connecting cable is formed of a bundle of wires. Therefore, multi-pole cables for probes have a large number of wires, and hence the connectors have a large number of contact terminals. Thus, the connectors should have a large size, while size compaction requirements urge for high miniaturization, resulting in weaker electric contact terminals and smaller distances between contact terminals.

Plug type connectors are used, in which the two connector members, i.e. the movable connector member at the end of the cable and the stationary connector member attached to a wall of the case of an apparatus, include a plurality of male engagement pin terminals projecting out of a support socket in parallel orientations, which engagement pins are designed for simultaneous engagement into respective female terminals of a plurality of female terminals in a corresponding socket, each of the female terminals having an engagement receptacle, the receptacles of the female terminals having axes parallel to one another, to the direction of engagement with the engagement pins and to the axes of the engagement pins, each engagement pin having an engagement receptacle axially coincident with said engagement pin.

In this case, the two connector members are mutually coupled by causing the male terminals and female terminals to be in axially coincident positions, electric contact being generated by simultaneously fitting all male terminals into all female terminals. Here, the axes of the male and female terminals are parallel to the engagement direction, and the two connector members are joined together and separated by such axial movement.

When the presence of a large number of terminals requires thinner male terminals, i.e. engagement pins, the latter are weakened to such an extent that they easily bend sideways and any minor misalignment during mutual engagement of the two connector members may cause damages to the connector, due to bending of one or more of said engagement pins. Also, the large number of these engagement pins and their considerable density per unit area of the support socket often prevents repair by simply straightening the bent engagement pins, because pin alignment tolerances are so strict that the working state is not easily restorable by manual means.

When an electric connector is required to have a large number of contact terminals, a so-called ZIF connector is known to be used. In this case, contact terminals are islands of conductive material insulated from each other and arranged in a predetermined pattern over a support header, which header also have conductive tracks for connecting each island of conductive material to a connection terminal, a wire or the like.

In these systems, used for instance for connection of processors to a circuit or in similar conditions, each the two connector parts consists of a terminal strip with a plurality of islands of conductive material, the patterns of conductive islands being identical on both terminal strips, and both terminal strips being held by support means which provide electric connection by laying and/or pressing the two terminal strips over and against each other with the patterns of conductive islands congruent with each other, wherefore each island of conductive material on the terminal strip of one of the two connector members contacts a corresponding island of conductive material on the terminal strip of the other connector member. The means for supporting the two terminal strips may be equipped with mechanical interlocking means, which may be separated, thereby affording releasable connection of the two connector parts. This type of connector provides the advantage that the islands of conductive material are not subject to deformation and hence, regardless of their size or density, there is no risk of damage to the male terminals. On the other hand, while the connector has a small size perpendicular to the terminal strips, such terminal strips still have a considerable surface area. This is a drawback in that when a large number of terminals are provided, the terminal strips and the terminal patterns have a considerable surface area, wherefore the terminals are prone to aggression and damage by foreign agents which easily penetrate to the surface of these contact terminals. Furthermore, since a part of the connector is designed to be stably supported by a case of the apparatus and particularly by a wall of such case, the wide surfaces of the terminal strips which support the terminals prevent any reduction of the case size, because at least one of the walls of this case is required to have a surface large enough to allow at least one connector to be attached thereto. This problem is even more important when two or more of these connectors have to be provided. The connector associated with the multi-pole cable also has a large size, and is thus of inconvenient and impractical use. Concerning the problem of the conductive islands being subject to fouling on their headers, the only solution in this case is the provision of covering or sealing elements on the open sides of the two connector parts. This makes the connectors even less practical, as well as more expensive, bulky and heavy.

In the above two types of prior art connectors, the two connector members are mechanically and electrically coupled together along a common axis, i.e. the two connector members are moved towards each other and mechanically coupled in a mechanical coupling direction that is parallel to the electric coupling direction and particularly the direction along which the electric contacts carried by the movable connector are fitted into the electric elements held by the stationary connector. This allows both mechanical and electric connections to be established and released together by the same movement.

The object of the present invention is to provide a multi-pole connector that can simply and inexpensively obviate the above drawbacks, while providing mechanical and electric connection between two connector members having a high density of electric contacts, without the risk of damaging such contacts during the frequent coupling and uncoupling operations required throughout the life of an apparatus connected by multi-pole cables to external elements for acquiring images, signals or the like and while maintaining low connector size requirements and making the use of connectors as simple and safe as possible in terms of possible damaging during use, of both the movable connector part and the stationary connector part.

The invention fulfils the above object by a multi-pole connector comprising a first movable connector member with a plurality of electric contacts supported by a terminal strip with a plurality of electric contact terminals thereon, in the form of electrically insulated islands of material arranged in a predetermined layout or geometrical pattern, which movable member is designed to be mechanically and electrically coupled to a second stationary connector member which has a terminal strip with a plurality of electrical contact terminals thereon, in the form of electrically insulated islands of material arranged in the same layout or geometrical pattern;

there being provided means for mechanically coupling the terminal strip of the movable connector member to the second connector member and means for mutual relative displacement of the terminal strip of the stationary connector member and that of the movable connector member, in a position of coincidence, with reference to the direction of displacement, of the contact terminal patterns on both terminal strips into a state of adhesion of the contact terminals of one terminal strip to those of the other terminal strip, the direction of mechanical coupling of the terminal strip of the movable connector member being parallel to said terminal strip and the direction of relative displacement of the terminal strip of the stationary connector member against the terminal strip of the movable connector member or vice versa being perpendicular to said terminal strip.

A preferred embodiment includes the following additional features:

the terminal strip of the movable connector member is supported in a cantilever projecting position by a case or socket of said movable connector member, in which case or socket the terminals of the wires of a multi-pole cable are electrically connected to respective conductive tracks for connection to a corresponding island of conductive material;

the terminal strip of the second stationary connector part being located behind a front wall of said second connector part, which front wall has an engagement slot for receiving the terminal strip of the movable connector member;

the terminal strip of the second movable member is offset from the receiving slot in a direction perpendicular to the extension of the latter parallel to the width of said terminal strip or of the long side of the slot delimiting edge;

said terminal strip of the stationary connector member is arranged to be oriented transverse, particularly perpendicular to said front wall and aligned with the slot in said front wall in a direction parallel to the width of the terminal strips and/or of the long side of said slot;

an engagement frame being provided, coincident with the receiving slot in said front wall, for receiving the terminal strip of the movable connector member, which frame is open on the side directly adjacent the slot and extends along a plane that passes through said aperture, wherefore the terminal strip is introduced into said frame through the receiving slot by a movement parallel to the surface of the terminal strip;

means being provided for centering the terminal strips of the stationary and movable connector members into a relative position in which each island of conductive material of the plurality of islands of conductive material on one of the terminal strips coincides with a corresponding island of conductive material of the plurality of islands of conductive material on the other of said terminal strips;

the terminal strip of the stationary connector member being supported in such a manner as to be able to move in a direction perpendicular to the frame that receives the terminal strip of the movable connector member, by the provision of manual displacement means, and said terminal strip of the stationary connector member having such a displacement stroke that said terminal strip is alternately displaced into a position in which it adheres against the terminal strip of the movable connector member within the frame and a position in which the terminal strip of the stationary connector member is away from the one of the movable connector member within the engagement frame.

Advantageously, mechanical displacement means are provided for displacement of the terminal strip of the stationary connector member, which are manually driven and are designed to be driven for displacing said terminal strip away from the terminal strip of the movable connector member when the latter is within the engagement frame, i.e. against said engagement frame, against the action of the elastic means that stably push the terminal strip of the stationary connector member against the terminal strip of the movable connector member within the engagement frame, i.e. against said engagement frame when the manually driven mechanical displacement means are in the disabled state, i.e. in the state in which the terminal strip of the stationary connector member is not displaced away from the engagement frame or the terminal strip of the movable connector member inserted in said frame.

The stationary connector member advantageously comprises a framework in which guides are provided for the displacement of the terminal strip of said stationary connector member, in a direction perpendicular to the front surface of said terminal strip, i.e. the surface having the plurality of islands of conductive material and in a direction perpendicular to an engagement frame which is fixedly secured to said framework in a position parallel to the terminal strip and coincident therewith in a direction of displacement thereof, whereas said framework further has elastic terminal strip-pushing means between the side of the terminal strip away from the engagement frame and a stationary stop on such side of the terminal strip and whereas the framework supports a mechanism for pushing and translating the terminal strip in the direction away from the engagement frame while counteracting the pushing action of said elastic means, members being further provided for driving said mechanism, which are susceptible of being seized by one hand and operated with such hand.

Concerning construction, the framework, the terminal strip guiding means, the displacement mechanism, the elastic means and the engagement frame may be constructed in any manner, according to any one of the appropriate construction options known and available to those of ordinary skill in the art.

The dependent claims and the description hereinbelow will discuss preferred construction embodiments that shall be intended without limitation to the general inventive concept.

The stationary connector member is constructed in view of allowing such stationary connector member to be provided in combination with the case of an apparatus, in which case the connector member is secured in the vicinity of a peripheral wall of said case, an aperture being formed in said case coincident with the position in which said stationary connector member is secured within said case.

The aperture may be the receiving slot itself, otherwise the aperture is closed by the front wall of the stationary connector member that is mounted to the framework, with the receiving slot being formed in such front wall.

In accordance with a preferred embodiment, the terminal strip of the movable member is fixed to a larger support plate, whose side edges oriented in the direction of engagement are shaped complementary to the branches oriented in the direction of engagement of the engagement frame. Thus provides an engagement guiding feature which also ensures accurate positioning of the terminal strip in its translation perpendicular to the engagement direction.

The above feature allows the two connector parts to have standardized sizes regardless of the actual dimensions of the terminal strip and/or the arrangement of the islands of conductive material. While the support plate shall always have the same size, the size of the terminal strip may change. Thus, while greater care is required when mounting the terminal strip to the support plate, this is a one-time operation.

The terminal strip of the stationary connector member may also have a support plate for the terminal strip proper to be secured thereto. In this case, the engagement frame has means for predetermined positioning of the support plate associated therewith. The presence of positioning means in a predetermined position always ensures coincidence between the terminal strip of the stationary member and that of the movable connector member as the latter is fully inserted in the engagement frame, regardless of the pattern and size of the terminal strips.

An additional apparent advantage is that, since the second connector part is located within the case and a slot is only required for connecting the movable connector to the stationary connector, any problem associated with cleaning or aggressions by foreign agents is obviated, and even the problems deriving from connector size requirements at the sides of the case where connectors have to be mounted and accessed are eliminated. Particularly, the connector-carrying sides of the case are conventionally the short sides of the shell, wherefore the presence of one or more connectors was a limit to size reduction in these sides, and prevented the construction of thin cases. Conversely, with the invention, terminal strip space requirements are parallel to the top and bottom sides of the case, whereas the space requirement perpendicular to the front and rear sides, i.e. the shell sides, is limited to the thin slot for receiving the terminal strip, possibly with the support plate, of the movable connector. This allows ZIF-type multi-pole connectors to be also used with portable ultrasound imaging apparatus, having a case of a size and shape similar to those of notebook or tablet computers. In the first step of engagement of the movable connector into the stationary connector, in which the terminal strip, or the support plate with the terminal strip associated therewith, is fitted into the engagement frame, the direction of engagement is similar to that of prior art connectors with plug contacts, and follows an axis of displacement parallel to the terminal strip or the support plate and perpendicular to the wall upon which the stationary connector part is mounted. Electric connection between the two terminal strips occurs within the case by moving said two terminal strips to contact, along an axis of displacement perpendicular to the terminal strips.

The provision of a mechanism for displacement of the terminal strip, with or without the support plate, in a direction perpendicular to the surface extension thereof, which mechanism has elastic means for pushing the terminal strip of the stationary connector member against the terminal strip of the movable connector member to full insertion into the engagement frame and means for displacement of said terminal strip of the stationary connector member away from the terminal strip in the engagement frame ensures a predetermined mutual compression of the islands of conductive material, i.e. the contact terminals of the two terminal strips and safe alignment of the terminal strips to ensure free insertion and free removal of the terminal strip of the movable connector member into and from the engagement frame.

Any type of mechanism may be used for displacement of the terminal strip of the stationary connector member.

In a preferred embodiment, the terminal strip is mounted, directly or via a support frame or plate, in such a manner as to slide or move parallel to itself along guides oriented perpendicular to the faces of the terminal strip, whereas the terminal strip and/or the support frame or plate are connected to a translation mechanism driven by a rocking control lever.

A particular embodiment of the translation mechanism consists in a rotating shaft mounted to the framework of the stationary connector member, which shaft is oriented perpendicular to the direction of insertion into the engagement frame and parallel to the faces of the terminal strip of the stationary connector member, and which shaft has a cam lying on the side of the terminal strip facing towards the engagement frame and facing away from the side of said terminal strip against which the elastic pushing means operate, which cam is designed with such a shape that a predetermined rotation of the shaft moves the terminal strip directly and/or via the support frame or plate to a position away from the engagement frame and hence from a terminal strip possibly received in said engagement frame in a contact position of the terminal strip of the stationary connector member against a terminal strip received in said engagement frame.

One embodiment of the cam may include a circular cam mounted to the shaft with its axis parallel to the axis of the shaft and with the axis of the shaft eccentric to the central axis of the circular cam.

One of the many options alternative to the above may include an elliptical cam with the drive shaft passing through one of the two centers of the elliptical base of the cam.

The shaft may be directly controlled by a rocking lever keyed to an end of the shaft, or there may be a rocking lever which is dynamically connected to the shaft through a transmission with a predetermined gear ratio and/or changes the orientation of the axis of oscillation of the lever relative to the axis of the shaft. The end of the shaft or the rocking lever support axis is in such position relative to the stationary connector member that said lever or other drive member may be mounted outside a front wall that delimits the connector and/or the case that contains it.

Advantageously, the engagement frame is provided in combination with means for stopping the stroke of the terminal strip of the movable connector member in the engagement frame of the stationary connector member, which means are in such position as to ensure that the terminal strip within the engagement frame and the terminal strip of the stationary connector member lie over each other with the islands of conductive material, i.e. the contact terminals on said two terminal strips, in perfect register, i.e. alignment with each other, with reference to the direction of displacement of said terminal strip of the stationary connector member.

According to yet another improvement, the terminal strip of the stationary connector member and the terminal strip of the movable connector member, or the engagement frame and/or the terminal strip supporting plates or frames on the corresponding connector member/s have complementary and cooperating centering means, which come into operation as the two terminal strips reach their mutual contact position.

According to a preferred embodiment, one or both terminal strips and/or support frames and/or support plates and/or the engagement frame have centering teeth or ridges which project perpendicular to the opposed sides of said plates and/or frames and are aligned with engagement holes, with reference to the direction of said plates or strips and/or said frames towards each other, said centering teeth or ridges being formed into a shape that tapers towards the free end, and particularly into a conical or frustoconical shape, whereas the smaller radius at the tip of said teeth or ridges is smaller than that of the corresponding hole and the larger radius at the base of said teeth or ridges is identical or slightly smaller than the radius of said holes.

This arrangement provides an automatic fine centering action as the two terminal strips of the two connector members reach their mutual contact state. In addition to the above, the terminal strip of the movable connector member is also mechanically locked in the engagement frame against removal thereof.

According to an improvement, the mechanical locking means preventing removal of the terminal strip of the movable connector member may also be separate means, other than the centering means and anyway these means may include a pin on the terminal strip of the stationary connector member or on the support frame or plate thereof, which pin cooperates with an engagement hole of the terminal strip of the movable connector member, said pin penetrating the hole during the stroke of the terminal strip of the stationary connector member towards that of the movable connector member in a state of full insertion in the engagement frame.

Further embodiments may be envisaged for said locking means, which may be totally separated from the terminal strip of the stationary connector member and are operated by the movement that drives the mechanism for displacement of said terminal strip.

The very small thickness of the connector of the invention allows two superimposed connectors to be provided, within the height and thickness dimensions of a case of an ultrasound imaging apparatus, i.e. the dimensions perpendicular to the larger top and bottom surfaces.

The particular construction of the connector, especially concerning the stationary connector member thereof, also allows integration of two separate, superimposed terminal strips, each terminal strip being combined with a parallel engagement frame for a cooperating terminal strip of a movable connector member, whereas the two terminal strips of the stationary connector member are mounted in such a manner as to be separately movable towards and away from the corresponding engagement frame, each of said terminal strips being associated with separate elastic means for pushing it against the corresponding engagement frame and separate drive means for displacement of each of said terminal strips away from it, which counteract the stable pushing action of the elastic means.

Like in the version with one terminal strip, in this dual terminal strip embodiment the terminal strips may be mounted in such an arrangement as to be able to slide along guides directly or via a support frame or a support plate, to, in or on which each terminal strip is fixed, whereas a separate mechanism for manually driving the displacement of the terminal strip is provided for each terminal strip and/or for each corresponding support frame or each corresponding support plate.

According to a preferred embodiment, the shaft and the common rotary drive member for said shaft may control two separate pushing members, each cooperating with a stop member for one of the two terminal strips or the corresponding support frame or the corresponding support plate.

In the above embodiment of the mechanism for driving the displacement stroke, the pushing means consisted of an appropriately shaped cam, and particularly an eccentric circular cam or an eccentric ellipsoidal cam. Here again the pushing means consist of a separate cam for each terminal strip.

Particularly, since the ultrasound imaging system operates with one probe at a time, the two cams may be keyed to a common shaft in angularly offset positions, so that the two terminal strips of the stationary connector member are alternately moved either into a position of contact with the terminal strip of a movable connector member with the latter being inserted in the corresponding engagement frame or into a position of maximum allowed distance from the terminal strip of a movable connector member with the latter being inserted in the engagement frame, so that, when one of the terminal strips of the stationary connector member is in the position in which it adheres against a terminal strip of a movable connector member within the engagement frame cooperating with said terminal strip of the stationary connector member, the other terminal strip of the stationary connector member is in the position of maximum allowed distance from the corresponding engagement frame and from a terminal strip of a movable connector member which is inserted in said engagement frame, whereas, by rotating the drive shaft through a predetermined relative offset angle of the two cams, said conditions is reversed, and the first terminal strip of the stationary connector member is moved into the position of maximum allowed distance from the associated engagement frame, whereas the other terminal strip of the stationary connector member is automatically moved to the contact position against a terminal strip of a movable connector member within the engagement frame associated therewith.

Due to this condition, the movable connectors of two different probes may be kept in mechanically restrained relation, with the corresponding stationary connector enabling and disabling electric connection, and hence alternately operating the probes, due to the displacement of the terminal strips obtained, as described above, by simply pivoting the displacement mechanism lever.

Means may be provided for temporarily retaining the lever in the angular position corresponding to each of the above two states, which lock the lever with a certain manually defeatable force in the angular positions corresponding to the electric connection operating states of either of the above probes. In practice, these means generate small clicks to indicate that either one of these two operating positions has been reached.

In view of the above, it will be appreciated that even more than two separate terminal strips may be provided within the same stationary connector member, each being associated with an engagement frame and being displaceable towards or away from such engagement frame using manual drive means. In this case, by the provision of a separate cam for each terminal strip, and synchronized operation of these cams according to a predetermined relative angular offset, the principle disclosed above with reference to the dual terminal strip arrangement may be further extended. Obviously, there will always be the option of providing a separate drive and displacement mechanism for each of the terminal strips within the stationary connector member, or allowing the terminal strips to be controlled in pairs by a common drive mechanism, which is constructed as described above, a separate displacement mechanism being provided for each pair of terminal strips of the stationary connector member.

An additional advantage of the present invention consists in that the terminal strip/s of the stationary connector member may have identical patterns of contact terminals, whereas the terminal strips of the movable connector members may have different patterns of contact terminals, in that not all the contact terminals need be present or active in the same pattern as on the terminal strips of the stationary connector member.

Further improvements of the invention will form the subject of the dependent claims.

The characteristics of the invention and the advantages derived therefrom will appear more clearly from the following description of a few non limiting embodiments, illustrated in the annexed drawings, in which:

FIG. 1 is a front side view of the stationary part of a connector of the present invention, in the embodiment in which two terminal strips are integrated in the same stationary connector member, the direction of view being parallel to the direction of insertion of the terminal strip of the movable connector member into an engagement frame and the font wall with the receiving slots being omitted, whereas the terminal strips of the stationary connector member are both spaced from the corresponding facing engagement frame and whereas the two engagement frames receive the terminal strips mounted on support plates of frames of two movable connector members.

FIG. 2 is a view similar to FIG. 1 showing the stationary connector member in which the upper terminal strip of the stationary connector member is in its contact position against the terminal strip of the movable connector member which is inserted in the upper engagement frame, whereas the lower terminal strip of the stationary connector member is in the position of maximum allowed distance from the terminal strip of an additional movable connector member which is inserted in the engagement frame immediately over said lower terminal strip.

FIG. 3 is a view similar to FIG. 1 showing a reversed operating state with respect to the one of FIG. 2, the upper terminal strip of the stationary connector member being in the position of maximum allowed distance from the terminal strip of the movable connector member which is inserted in the upper engagement frame, whereas the lower terminal strip of the stationary connector member is in its contact position against the terminal strip of an additional movable connector member which is inserted in the engagement frame immediately over said lower terminal strip.

Figure 1:
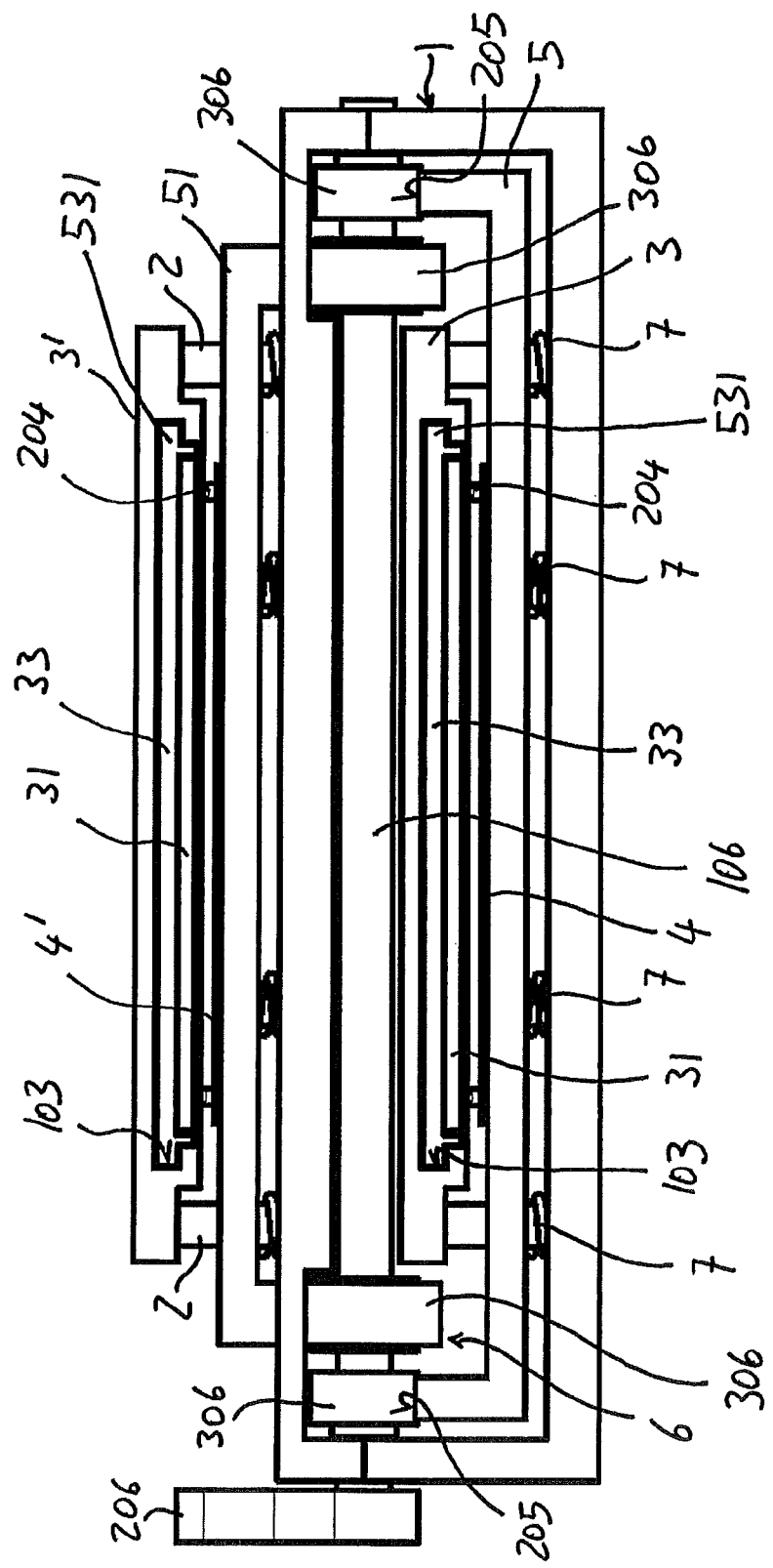
Figure 2:
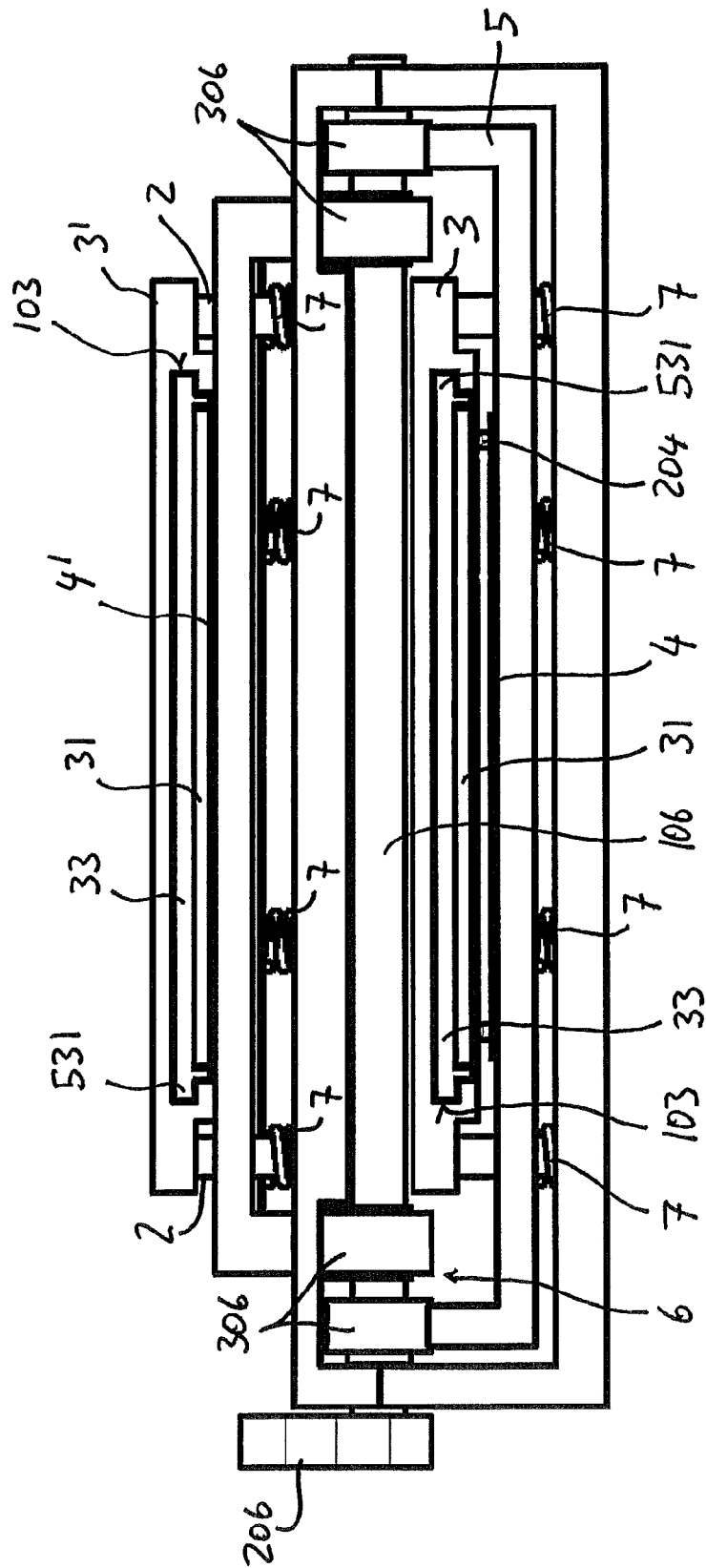
Figure 3:
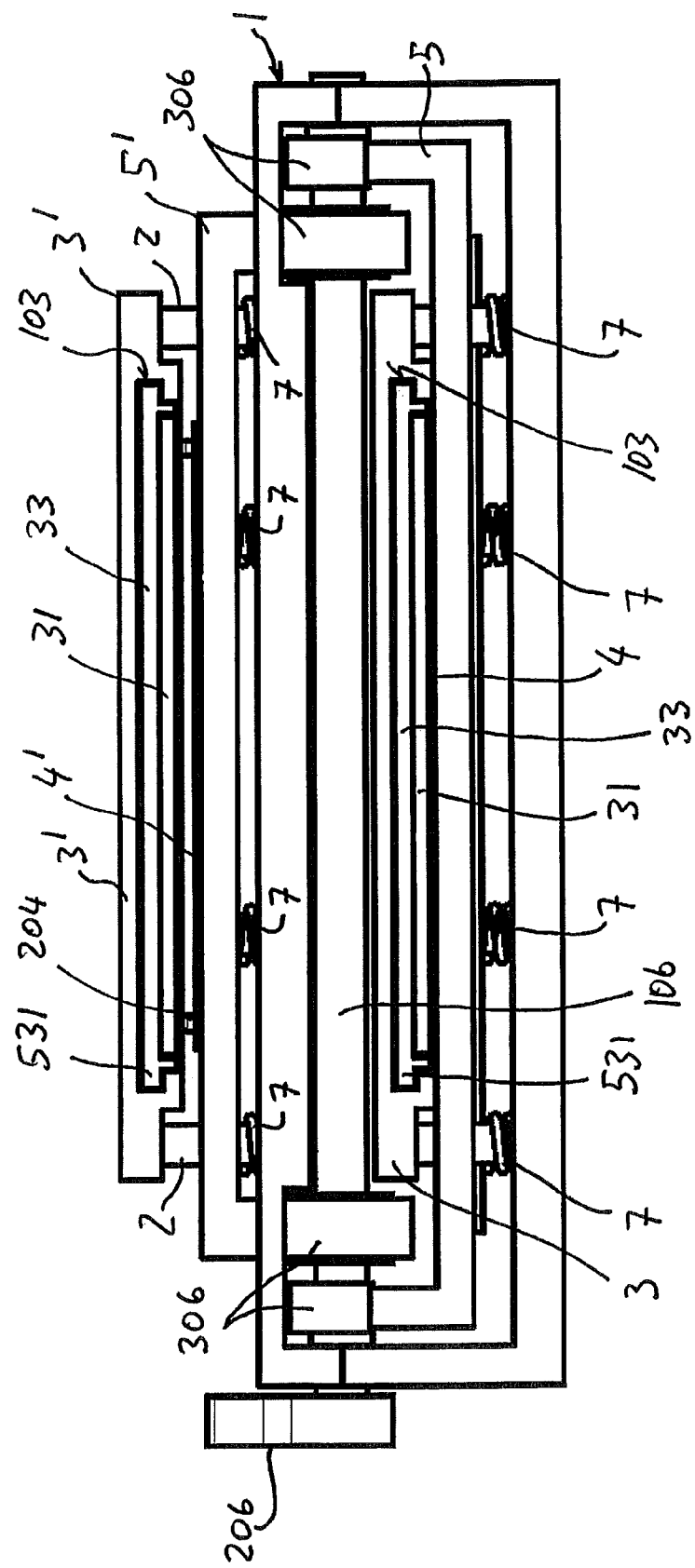

FIGS. 7A, 7B, 8A, 8B and 9A, 9B are, respectively, a front view similar to FIGS. 1 to 3 showing the stationary connector member, the frames thereof receiving the terminal strips of two movable connector members, and a side view of said stationary connector member with the two movable connector members coupled thereto and with the terminal strips of the stationary connector member in the three different positions corresponding to those of FIGS. 1 to 3.

Figure 10:
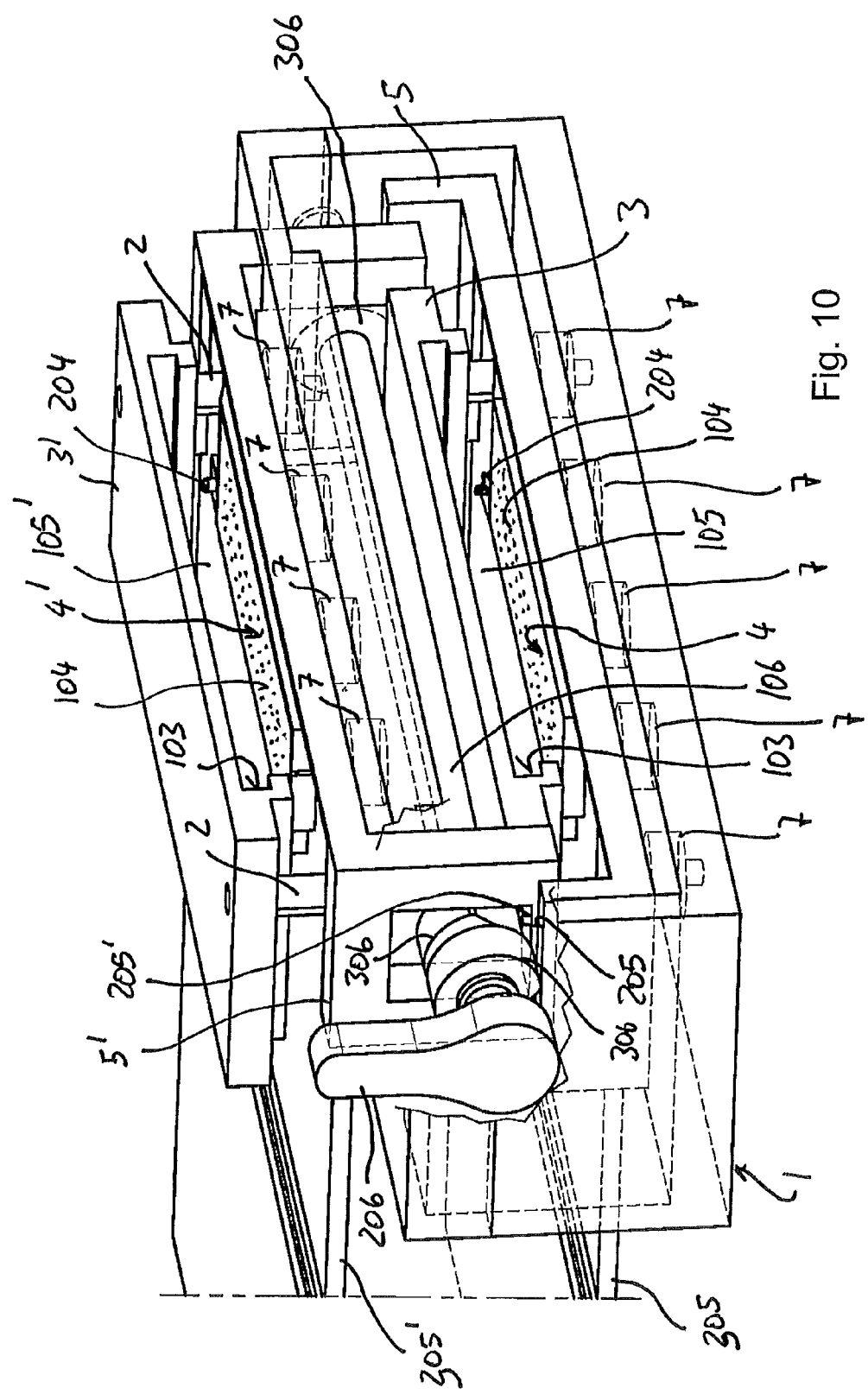

FIG. 10 is a partially transparent and perspective view of the stationary connector member, showing the mechanism for displacing the terminal strips and the elastic means for pushing them against the facing engagement frame.

The illustrated embodiment relates to a connector configuration in which the stationary connector member has two terminal strips, each having, associated thereto, an engagement frame for a terminal strip of a movable connector member, two movable connector members being allowed to be coupled to said double stationary connector member. While the illustrated embodiment with such double stationary connector member is preferred, an embodiment may be also provided in which the stationary connector member has a single terminal strip associated with a single engagement frame for the terminal strip of a movable connector member.

The construction of this single stationary connector member can be derived from that of the double element in a manner that is known to those skilled in the art by simply removing the second terminal strip with the second engagement frame and the second cam for displacement of the second terminal strip from the illustrated structure.

Likewise, the construction of the stationary connector member may include three or more pairs of terminal strips and engagement frames and as many means for displacement of each terminal strip.

As already mentioned in the introduction, separate displacement means may be provided for each terminal strip or, like in the solution with two terminal strips, there may be either a single mechanism operating alternately and/or sequentially on the terminal strips or a mechanism as shown herein for each pair of terminal strips.

The mechanisms, the framework, the guides and the other construction elements may be also embodied in various forms, in the context of the ordinary base knowledge of those skilled in the art.

Referring to FIG. 10, the stationary connector member comprises a framework 1 with an open front side, in which a pair of posts 2 are mounted at two opposite sides of the framework 1. The two posts support two engagement frames 3, 3' in stable positions and at predetermined distances from each other, each being designed to receive a terminal strip 31 of a movable connector member 30 (see FIGS. 4 to 9).

The two engagement frames 3, 3' have respective slide guides 103 along the two opposed sides oriented perpendicular to an open receiving side and parallel to each other and to the direction of insertion of a terminal strip 31 in said engagement frame 3, 3'. The back side opposite to the open side is closed and acts as a stop abutment for a terminal strip introduced in said engagement frame 3, 3'.

Each of the two engagement frames 3, 3' lies over a terminal strip 4, 4'. Each of these strips has a plurality of electric contact terminals 104 in the form of islands of conductive material arranged in a predetermined pattern over the surface of the terminal strip 4, 4' facing towards the associated engagement frame 3, 3'. Each terminal strip 4, 4' is carried by a support frame 5, 5'. The support frames are slideably mounted to the posts 2, which act, in this case, as slide guides for said support frames 5, 5'. The posts 2 are oriented perpendicular to the plane defined by the engagement frames 3, 3' and the faces of the terminal strips 4, 4'. Any construction may be provided for the support frames 5, 5'. In a preferred and advantageous embodiment, each support frame 5, 5' has a bearing structure composed of crossbars and posts, which carries a support plate 105, 105'. The support plates 105, 105' are designed to carry the terminal strips 4, 4' and, in an advantageous embodiment, are also equipped with wires for connection of the corresponding terminal strips 4, 4' to the processing circuits. In this embodiment, the terminal strips 105, 105' have a plurality of conductive tracks, each for a contact terminal of the corresponding terminal strip 4, 4' and which conductive tracks are separately connected, by usual electric connection means, to as many input channels of a processing circuit.

The sides of each support frame 5, 5' for the terminal strips 4, 4', opposed to the engagement frames 3, 3' are acted upon by elastic pushing elements for pushing each support frame 5, 5', and hence the terminal strip 4, 4' carried thereby, towards the corresponding engagement frame 3, 3' and which means stably push each support frame 5, 5' towards the corresponding engagement frame 3, 3'. As described in greater detail below, the stroke is so designed that, when a terminal strip 31 of a movable connector member 30 is inserted in the engagement frame 3, 3', then the elastic pushing means operate to cause the terminal strip 4, 4' on the support frame 5, 5' or the support plate 105, 105' to adhere against a terminal strip 31 of a movable connector member 30 inserted in the engagement frame 3, 3'.

A mechanism 6 for displacement of the support frames 5, 5' comprises a shaft pivotally mounted in the framework 1. One end of the shaft external to the framework carries a driving lever 206, whereas two cams 306 are mounted to the shaft 106 in axially adjacent positions, each for cooperation with a push surface 205, 205' of one of the two support frames 5, 5'.

The cams 306 have such a shape that the rotating shaft 106 alternatively causes the support frame 5, 5', with the terminal strip thereon, to move away from the corresponding engagement frame 3, 3' against the action of the elastic pushing means 7 and the support frame 5, 5' to move into the position of contact with a terminal strip 31 of a movable connector member 30 inserted in the engagement frame 3, 3', due to the same elastic pushing means 7.

The elastic pushing means 7 are interposed between the side of the support frame 5, 5' away from the engagement frame 3, 3' and a transverse abutment wall 101. Particularly, in the illustrated embodiment, the elastic pushing means 7 act upon the side of the support plate 105, 105' away from the side with the terminal strip 4, 4'.

The elastic pushing means 7 are helical springs, two of which are fitted onto a respective post 2.

Each of the terminal strips 4, 4' carries a centering pin 204 oriented in the direction of the displacement stroke of the support frames 5, 5', and hence the terminal strips 4, 4', the axis of such pin 204 being parallel to the axes of the posts 2. Preferably, each terminal strip 4, 4' has a pair of centering pins 205 at the corner areas of the side transverse to the direction of insertion into the engagement frame 3, 3'. These centering pins 204 have a tapered end, particularly of conical shape, and are designed to cooperate with coincident holes 32 of a terminal strip 31 of a movable connector member 30, when such terminal strip 31 is inserted in the engagement frame 3, 3' in the fully inserted position, i.e. with the transverse side 231 of said terminal strip 31, with reference to the direction of insertion, which transverse side 231 abuts against the transverse side of the engagement frame away from the open receiving side. In the end section of the stroke of one of the terminal strips 4, 4' of the stationary connector member towards the terminal strip 31 of the movable connector member 30 inserted in the associated engagement frame 3, 3', the centering pins 204 penetrate the holes 32, the tapered end allowing fine relative adjustment of the two terminal strips 4, 4' and 31 so that each of the islands of conductive material 131 of the terminal strip 31 of the movable connector member 30 contacts a corresponding island of conductive material of the terminal strip of the stationary connector member. It shall be noted that the islands of conductive material on the terminal strips 4, 4' and 31 are of relatively high density, which means that these islands are very small and spaced as closely as possible, wherefore fine adjustment of the relative alignment of the terminal strips 4, 4' of the stationary connector and the terminal strips 31 of the movable connectors 30. It shall be further noted that, still considering an identical pattern of islands of conductive material 104, 131 on the terminal strips 4, 4', 31 of the stationary connector member and the movable connector member respectively, the terminal strips 4, 4', 31 may include only some of the islands of conductive materials 104, 131 of the pattern or some of these islands of conductive material have no wire connected thereto, depending on the type of probe or electronic circuit being used. This affords standardization of at least the pattern of islands of conductive materials 104, 131 and possibly the whole terminal strip configuration, regardless of the number of contacts required by each particular probe and/or electronic circuit.

Concerning the driving mechanism, the cams 306 have such a shape that, upon rotation of the shaft 106 caused by the lever 206, each of said two cams alternately pushes, against the action of the elastic means, the corresponding support frame 5, 5' of a terminal strip 4, 4' progressively to a position of maximum allowed distance from the engagement frame 3, 3' and allows the progressive sliding motion of the corresponding support frame 5, 5', and hence the terminal strip 4, 4' towards the associated engagement frame to a contact position between the terminal strip 4, 4' of the stationary connector member and a terminal strip 31 of a movable connector member 30 with the latter inserted in the engagement frame 3, 3', the sliding motion in said direction towards the engagement frame being caused by the pushing action of the elastic means 7 upon the corresponding support frame 5, 5' against the stopping action performed by the cams on said support frame 5, 5'.

The above construction features are also confirmed by FIGS. 1 to 9.

Figure 4:
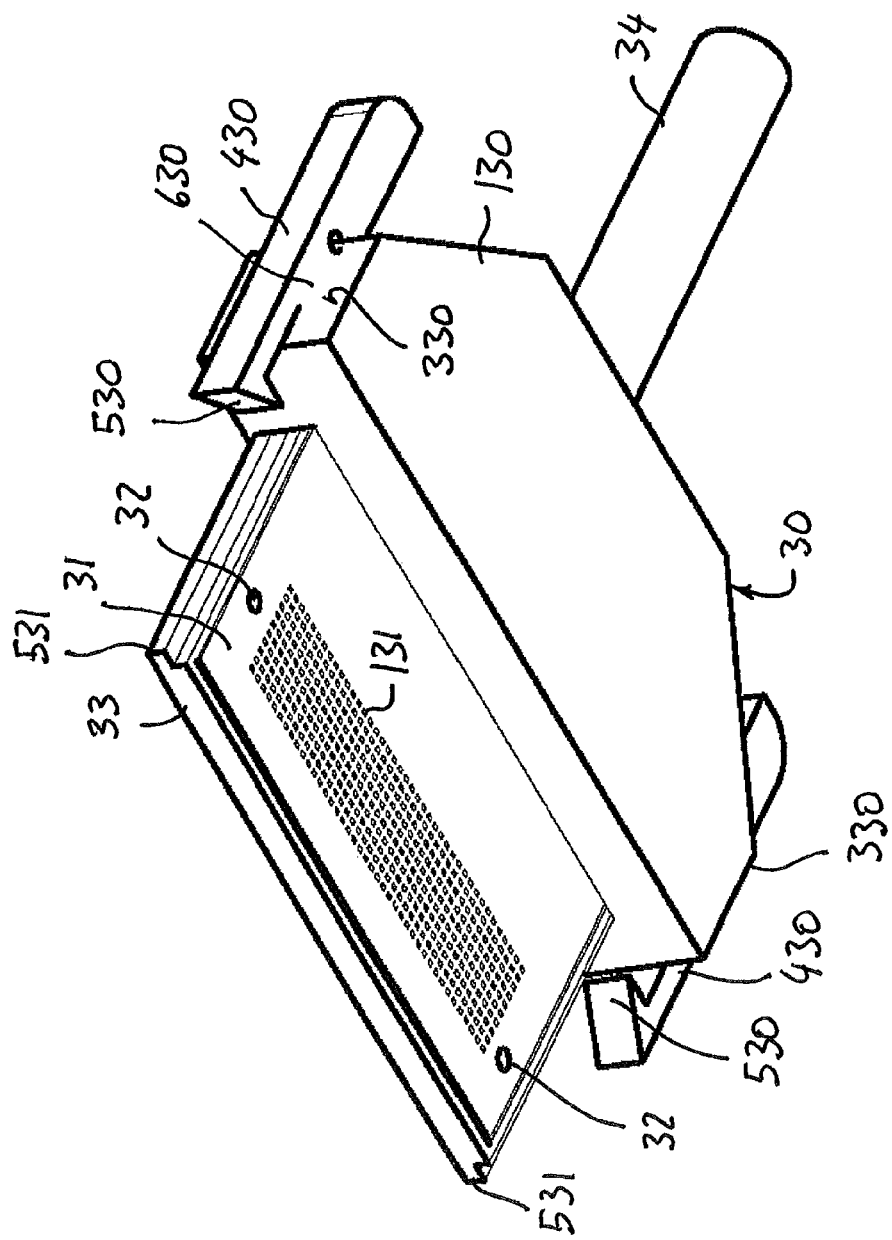
FIG. 4 is a perspective view of a movable connector member, with a multi-pole cable extending therefrom for connection to a probe.

Particularly, FIG. 4 is a perspective view of the movable connector member 30 which comprises a case 130 with an access for a multi-pole cable 34, a terminal strip 31 overhanging the opposite side of the case. This terminal strip is oriented parallel to the axis of the multi-pole cable 34 at the access hole of the case 130. The terminal strip 31 is advantageously mounted to a support frame 33 or a support plate which overhangs the case 130 and ends with one end therein. The case 130 contains the electric connections between the terminals of the wires of the multi-pole cable 34 and the islands of conductive material of the terminal strip 31. This may occur in various manners. According to a first alternative, the terminal strip 31 may have a plurality of conductive tracks on the side away from the one with the conductive islands 131, each track being electrically connected to a corresponding conductive island 131 and each track ending at the edge of the terminal strip 31 (not shown in detail, like the conductive tracks) which is at the end of the terminal strip 31 inside the case 130 of the movable connector member.

Otherwise, the conductive tracks are formed on the support frame or plate 33, each of the islands of conductive material of the terminal strip 31 being connected to one of said conductive tracks. This may occur in various manners, such as by providing conductive islands that extend throughout the terminal strip 31, with said islands of conductive material being in contact, on the side adhering against the support frame or plate 33, with a corresponding island of conductive material that forms the terminal of a conductive track on said support frame or said support plate 33. In this case, the pattern of islands of conductive material on the support frame or support plate 33 is identical to and coincident with the pattern of islands of conductive material 131 on the terminal strip. By this arrangement, the terminal strip 31 may be easily replaced without requiring connection of all the wires of the multi-pole cable. This is a complex and burdensome operation, that can only be performed by a machine, due to the high density of the terminals for connection to the wires of the multi-pole cable.

Instead of providing a simple contact-type connection between the contact terminals of the support frame or support plate 33 and the islands of conductive material of the terminal strip 31, each island of conductive material 131 may be arranged to extend towards the support frame or plate 33 via a contact pin, which is designed to be pressed into engagement with a corresponding tubular terminal on the support frame or plate.

Other solutions will be envisaged by those of ordinary skill in the art, using known configurations of electric connectors.

The above construction for connection of the islands of conductive material to the wires via conductive tracks on the support frame or support plate or on the back of the terminal strip requires no essential change to the terminal strips 4, 4' and the corresponding support frames or plates 5, 5' of the stationary connector member for connection of the islands of conductive material 104 of these terminal strips 4, 4' with the electronic circuits of the apparatus, in this case an ultrasound imaging apparatus.

Figure 5:
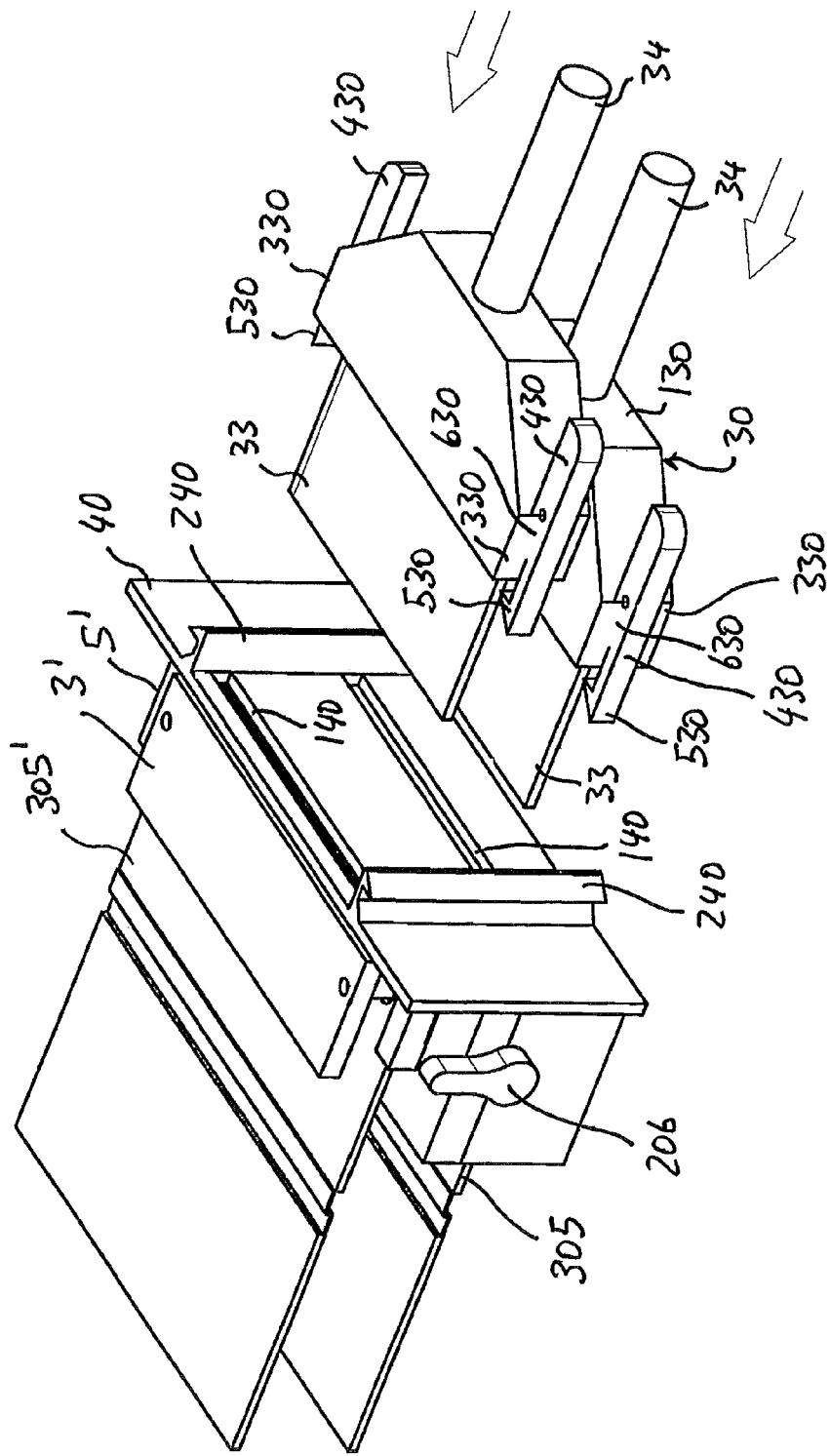
FIG. 5 is a perspective view of the stationary connector member of the previous figures and two movable connector members ready to be coupled to the stationary connector member, with their terminal strips ready to be inserted into one of the two engagement frames of the stationary connector member respectively.
Figure 6:
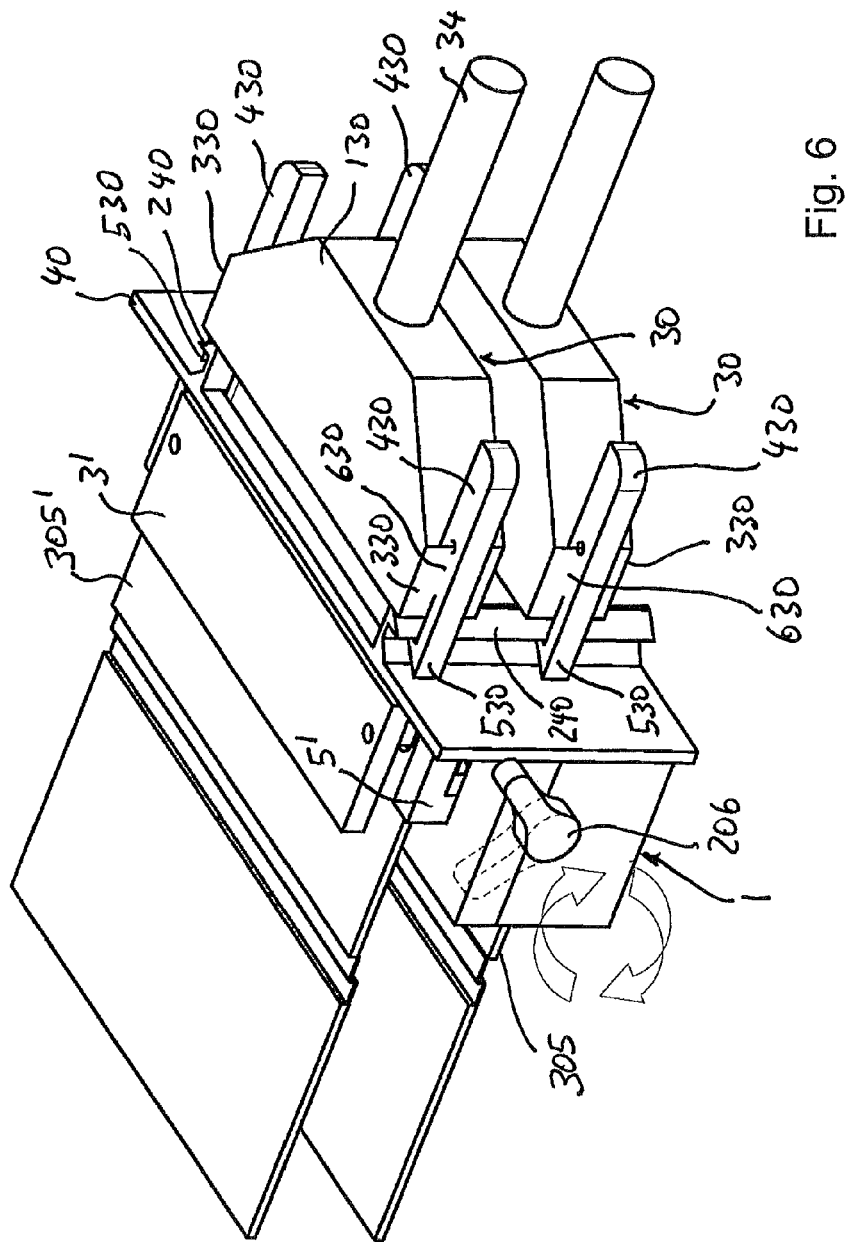
FIG. 6 is a view similar to FIG. 5, in which the two movable connector members are coupled to the double stationary connector member, the terminal strips of said two movable connector members being inserted in the two engagement frames of the double stationary connector member.

Referring now to FIGS. 5 and 6, the stationary connector member is mainly designed to be mounted inside a case of an apparatus with which a device has to be connected by said connector. Namely, the apparatus is an ultrasound imaging apparatus and the device is a scanning probe of said apparatus. For this purpose, the stationary connector member is provided in combination with a front covering wall 40 (with reference to the direction if insertion of the terminal strip 31 of the movable connector member 30 into the engagement frame 3, 3'). Such front cover wall 40 has a receiving slot 140 coincident with the transverse open receiving side of engagement frame 3, 3', through which the terminal strip 31 of a movable connector member 30 is introduced into one of the two engagement frames 3, 3'.

This front wall may consist of a part of the wall that is fixed to the framework 1 of the stationary connector member, like in the case of add-on boards in personal computers which have, in addition to the PCB, a transverse plate for closing an aperture in the case, which aperture is coincident with the PCB mounting position in the connector for the motherboard and which closing plate also carries the stationary connector members for the ports designed for such boards.

Otherwise, the front wall is one of the side walls of the case that contains the circuits of the apparatus and the wall includes the two slots 140 in a predetermined position relative to the predetermined position of the stationary connector member.

According to yet another advantageous characteristic, removable means are provided between the movable connector member 30 and the stationary connector member for mechanically locking one of said two connector members to the other. These means may be constructed in any manner. Particularly, these means are accessible from outside, are manually operable and provide mechanical connection of the case 130 of the movable connector member to the framework of the stationary connector member and/or the front wall 40.

These means may be screw means, such as those used in serial or parallel connectors or in VGA connectors of PC monitors or may be interlocking means like those used for the so-called "centronics" connectors for parallel connection of printers or the like.

Referring to the illustrated embodiment, the case 130 of the movable connector member has an elastically swinging tongue 430, on each side 330 oriented in the direction of insertion of the terminal strip 31 and perpendicular to said terminal strip 31. Each tongue 430 is oriented in the direction of insertion of the terminal strip 31 into the engagement frame 3, 3' and has a hook-like tooth 530 at the end facing towards the stationary connector member, which projects on the side of said tongue facing towards the terminal strip 31. The opposite end of the tongue projects out of said side 330 of the case with which it is joined, at a tapered area of the case 130. The tongues are fixed to the corresponding sides 330 of the case 30 by a bridge of material 630, which is elastically flexible and allows oscillation for opening apart the ends of the two tongues that carry the teeth 530, the action of bringing the latter towards each other being manually exerted upon the ends of the tongues away from those with the teeth 530, whereas said bridges of material 630 allow the two tongues to elastically return to their parallel rest positions, in which their teeth 530 are close to each other. The teeth have a saw tooth profile, with an inclined surface on the side facing towards the direction of insertion of the terminal strip 31 into the corresponding engagement frame 3, 3'.

Hook-like means 240 are provided on the front wall 40 in line with each tooth 530. In the illustrated embodiment, the hook-like means 240 include a rib formed on the outer side of each of the two opposite ends of the receiving slots 140, which is oriented perpendicular to the longitudinal extension of said slots 140. These ribs have a cross section substantially identical to that of the teeth 530 but rotated through 180° relative to them, wherefore the projection faces away from them. Due to the provision of the opposed inclined faces, as the terminal strip 31 of a movable connector member 30 is inserted into the corresponding engagement frame 3, 3', the inclined front faces of the teeth 530 of the tongues 330 come into cooperation with the complementarily inclined front face of the hook-like ribs 240 which automatically cause the tongues 330 to open apart, and the teeth 530 to be coupled to the hook-like ribs 240. For the movable connector 30 to be released, the ends of the tongues 330 with the teeth 530 have to be opened apart into the position of disengagement of these teeth from the hook-like ribs 240 by drawing the opposite ends of the tongues 330 towards each other, whereupon the movable connector member 30 can be moved away.

A further construction feature that appears from the figures is that the sides of the engagement frames 3, 3' oriented in the direction of insertion have a L section. Each of said sides oriented in the direction of insertion has a longitudinal groove 103 formed on the face that faces towards the interior of said engagement frame 3, 3' and towards the opposed side. The corresponding side edges of the terminal strip 31 or the support frame or support plate 33 have a shape that matches that of the sides of the engagement frames 3, 3', i.e. with a longitudinal lateral tab 531 adapted to be inserted into the groove 103 of the corresponding side of the engagement frame 3, 3'. By this arrangement, the terminal strip 32 or the support frame or plate 33 thereof are firmly held in position within the engagement frame, with reference to a direction of displacement parallel to the stroke of the terminal strip 4, 4' of the stationary connector member towards it. This is an important feature, in that it allows the elastic pushing members to bring the two terminal strips 4, 4' and 31 of the stationary connector member and the movable connector member respectively into mutual contact while ensuring a predetermined compression force between the two strips, and hence ensuring that the characteristics of electric contact between the islands of conductive material are within the limits of optimal electric conduction and are repeatable within specified tolerances.

According to an additional advantageous feature, the means for displacement of the support frames 5, 5', and hence the terminal strips 4, 4' of the stationary connector member may have such a shape that three operating states of the stationary connector member may be provided, as particularly shown in FIGS. 1 to 3 and 7 to 9, which operating states correspond to a first condition in which both terminal strips 4, 4' are spaced from the terminal strip 31 of a movable connector member inserted in the engagement frame 3, 3' associated with said terminal strip 4, 4' of the stationary member, and two operating conditions alternative to each other and to said first operating condition, in which latter operating conditions either a first terminal strip 4 of the stationary connector member is moved to contact against the terminal strip 31 of a movable connector member 30 with the latter being inserted in the engagement frame 3 associated with said first terminal strip 4 of the stationary connector member, while the second terminal strip 4' is spaced from the terminal strip 31 of a movable connector member 30 which is inserted in the engagement frame 3' associated with said second terminal strip 4' of the stationary connector member, or a second terminal strip 4' of the stationary connector member is moved to contact against the terminal strip 31 of a movable connector member 30 with the latter strip being inserted in the engagement frame 3' associated with said first terminal strip 4' of the stationary connector member, while the first terminal strip 4 is spaced from the terminal strip 31 of a movable connector member 30 which is inserted in the engagement frame 3 associated with said first terminal strip 4 of the stationary connector member.

The particular construction of the stationary connector member provides considerable advantages in view of achieving these operating conditions, that are shown in FIG. 1, FIG. 2 and FIG. 3 respectively, as well as in FIG. 7, FIG. 8 and FIG. 9.

Particularly the two cams 306 mounted to the rotary drive shaft 106, each cooperating with the support frame 5, 5' of one of the two terminal strips 4, 4' are angularly offset from each other and have such a shape that the two support frames 5, 5' and hence the strips 4, 4' may be moved in the above described positions, i.e. either with both strips spaced from the engagement frames 3, 3' and hence from the terminal strip 31 of a movable connector member 30 within said engagement frame 3, 3' or with one of the terminal strips 4, 4' alternately spaced from and in contact with the terminal strip 31 of a movable connector member within the associated engagement frame 3, 3' and with the other of the two strips being automatically moved into contact against and spaced from the terminal strip 31 of a movable connector member within the associated engagement frame 3, 3'.

Particularly, these cams 306 may be circular cams eccentrically mounted to the rotary drive shaft 106 with an angular offset of 180° from each other. Otherwise, the cams 306 may have an elliptical shape, with the axis of rotation passing through one of the two centers of their elliptical shapes.

As particularly shown in FIGS. 7, 8 and 9, the lever for rotatably driving the shaft is in such an angular position relative to the cams that the condition in which both terminal strips 4, 4' of the stationary connector member are simultaneously spaced from the associated engagement frame 3, 3' or from the terminal strip of the movable connector member 30 inserted therein is achieved when the driving lever is in an intermediate position between two opposite angular positions, which two end positions are such that one of said end positions of the lever corresponds to the condition in which one of the two terminal strips 4 is spaced from the terminal strip 31 of a movable connector member within the associated engagement frame 3, while the other of said two terminal strips 4' is in contact with the terminal strip 31 of a movable connector member within the associated engagement frame 3', and the other of the two end positions of the lever corresponds to the condition in which one of the two terminal strips 4, 4' is in contact with the terminal strip 31 of a movable connector member within the associated engagement frame 3, 3', while the other of the two strips is spaced from the terminal strip 31 of a movable connector member within the associated engagement frame 3, 3'.

In the intermediate position the two cams are oriented with the radius that passes through the axis of the rotary drive shaft 106 parallel to the terminal strip, whereas in the other two positions the two cams are oriented with the radius that passes through the axis of the rotary drive shaft 106 perpendicular to the terminal strips and alternately with the radially outermost part towards the engagement frame 3, 3' associated with one of the two terminal strips 4, 4'.

Particularly referring to FIGS. 5 and 9, since both terminal strips 4, 4' may be simultaneously spaced from the corresponding associated engagement frame 3, 30, two movable connector members 30 may be coupled to a common stationary connector member, without enabling electric connection of the two connector elements, i.e. without bringing the corresponding terminal strips 4, 4' and 31 into mutual contact. Thus, each of the two engagement frames 3, 3' may receive the terminal strip 31 of a movable connector member 30, and since both movable connector members are mechanically coupled to the stationary connector member at the same time, only mechanical connection is initially established between the movable connector members and the stationary connector member, electric connection not being enabled for none of the two movable connector members.

The provision of the removable mutual locking means as described above in greater detail, which are provided on the cases 130 of the movable connector members 20 and on the front wall 40 attached to or integral with the framework of the stationary connector member allows the movable connector members 30 to be mechanically held against the stationary connector member.

Figure 7A:
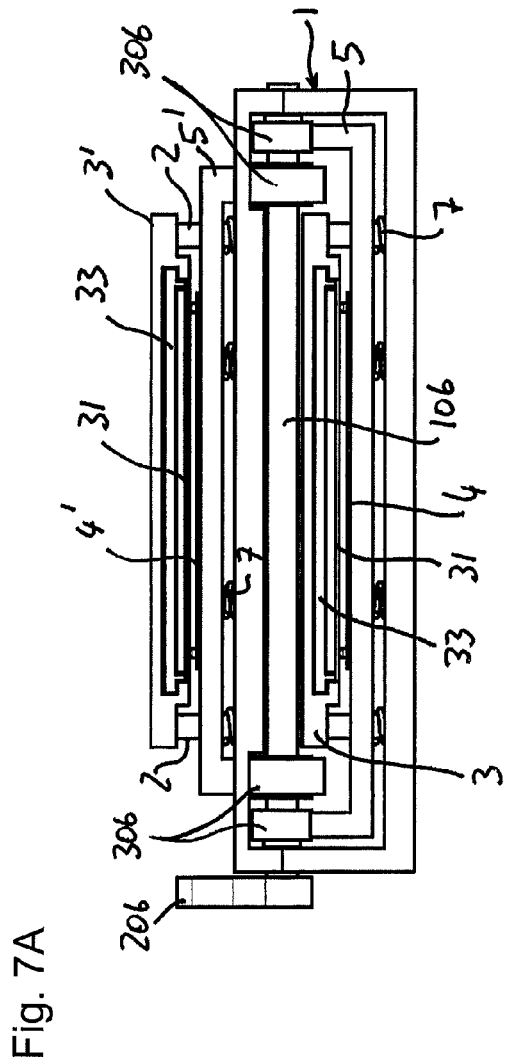
Figure 7B:
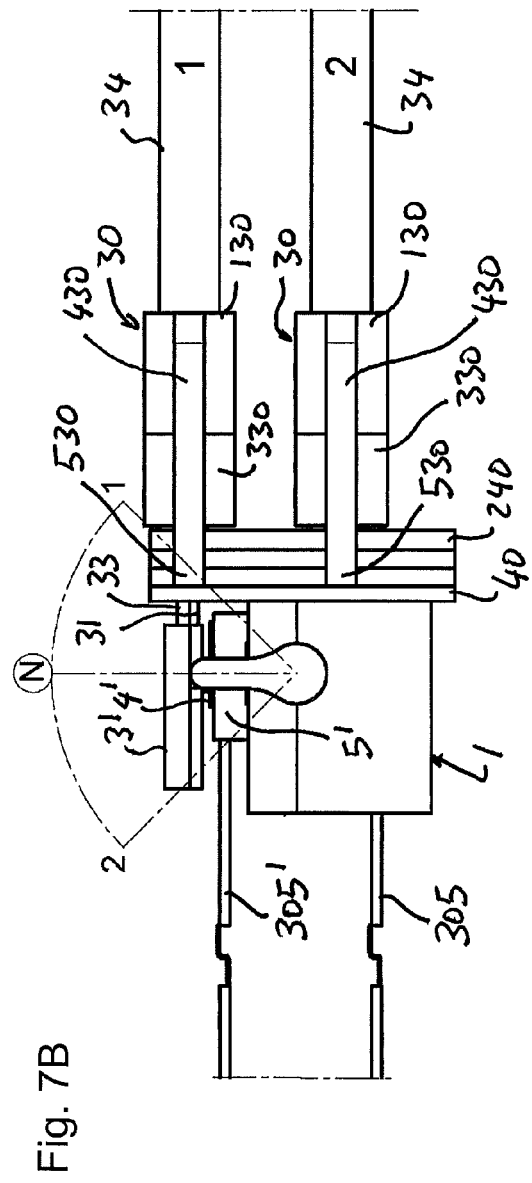

FIGS. 1, 7A and 7B show the condition in which both terminal strips 4, 4' of the stationary connector member are spaced from the corresponding engagement frame 3, 3' containing the terminal strip 31 of a movable connector member 30 attached to the stationary connector member using the above means. The lever 206 is in an intermediate vertical position, the letter N designating a neutral electric connection condition, i.e. the lack of electric connection for both movable connector members 30.

When the lever is pivoted into the position 1 (see FIGS. 2, 8A and 8B), the cams 306 are rotated into such a position that the upper terminal strip 4 of the stationary connector member is pushed against the terminal strip 31 of the movable connector member 30 which is inserted in the associated upper engagement frame 3. Conversely, the lower terminal strip 4' is spaced from the lower engagement frame 3', and hence from the terminal strip 31 inserted in said engagement frame 3', which is part of a second movable connector member 30. Therefore, in this condition, electric contact is established between the stationary connector member and the upper movable connector member 30, i.e. between their respective terminal strips 4 and 31, whereas the lower movable connector member is only mechanically coupled to the stationary connector member, with no electric contact being established therebetween, i.e. the terminal strips 4' and 31 are electrically insulated from each other.

FIG. 3 and FIGS. 9A and 9B show a condition opposite to the above. In this case, the lever 206 is pivoted into the opposite end position, designated by numeral 2. As shown in FIGS. 9A and 3, the cams 306 are rotated into such a position that the lower terminal strip 4' of the stationary connector member is pushed against the terminal strip 31 of the lower movable connector member 30 which is inserted in the associated lower engagement frame 3'. Conversely, the upper terminal strip 4 is spaced from the upper engagement frame 3, and hence from the terminal strip 31 inserted in said engagement frame 3. Therefore, in this condition, electric contact is established between the stationary connector member and the lower movable connector member 30, i.e. between their respective terminal strips 4' and 31, whereas the upper movable connector member is only mechanically coupled to the stationary connector member, with no electric contact being established therebetween, i.e. the terminal strips 4 and 31 are electrically insulated from each other.

By this feature, two movable connector members of two probes may be held physically connected by mechanical means, the lever 206 being simply pivoted to enable either one of such probes or disable both, by enabling or disabling electric contact between the movable connector members and the stationary connector member.

Finally, the lever 206 is shown to be directly mounted to the rotary drive shaft 106 for the cams 206. Nonetheless, the axis of rotation of the lever may be deviated from the axis of the shaft 106, by the provision of appropriate elbow joints or angle drives, wherefore the lever may be arranged to rotate about an axis perpendicular to the front wall 40, so that both the receiving slots 140 and the lever 206 may be located on the same side of the ultrasound imaging apparatus or the like.

The invention claimed is:

1. A multi-pole connector comprising:
   a first movable connector member with a plurality of first electric contact terminals supported by at least one terminal strip, said first electric contact terminals being defined by electrically insulated islands of material arranged in a predetermined layout or geometrical pattern, said movable member being designed to be mechanically and electrically coupled to a second stationary connector member which has at least one terminal strip with a plurality of second electric contact terminals thereon, in the form of electrically insulated islands of material arranged in the same said predetermined layout or geometrical pattern;
   means for mechanically coupling the terminal strip of the movable connector member to the second connector member and means for mutual relative displacement of the terminal strip of the stationary connector member and the terminal strip of the movable connector member, in a position of coincidence, with reference to the direction of displacement, of the contact terminal patterns on both terminal strips into a state of adhesion of the contact terminals of one terminal strip to those of the other terminal strip, the direction of mechanical coupling of the terminal strip of the movable connector member being parallel to said strip and the direction of relative displacement of the terminal strip of the stationary connector member against the terminal strip of the movable connector member or vice versa being perpendicular to said terminal strip;
   an engagement frame for the terminal strip of the movable connector member provided above the terminal strip of the stationary connector member, which frame is open on a receiving side, wherefore the terminal strip of the movable connector member is introduced into said engagement frame by a movement parallel to the surface of the terminal strip;
   means for mutually centering the terminal strips of the stationary member and the movable member of the connector into a relative position in which each island of conductive material of the plurality of islands of conductive material on one of the terminal strips coincides with a corresponding island of conductive material of the plurality of said islands of conductive material on the other of said terminal strips; and
   a case for the movable connector member, which case has at least one wall that at least partially closes one side or one aperture in one side of said case and that has a slot allowing insertion of a movable connector member into the engagement frame of the stationary connector member, which slot is coincident with the open side of said engagement frame;
   wherein the terminal strip of the stationary connector member is supported in such a manner as to be able to move in a direction perpendicular to the frame that receives the terminal strip of the movable connector member, by the provision of manually driven displacement means; and
   wherein said terminal strip of the stationary connector member having such a displacement stroke that said terminal strip is alternately displaced into a position in which it adheres against the terminal strip of the movable connector member within the engagement frame and a position in which the terminal strip of the stationary connector member is away from the terminal strip of the movable connector member within the engagement frame.

2. A connector as claimed in claim 1, wherein the terminal strip of the movable connector member is supported in a cantilever projecting position by a case or socket of said movable connector member, in which case or socket the terminals of the wires of a multi-pole cable electrically connected to respective conductive tracks for connection to a corresponding island of conductive material.

3. A connector as claimed in claim 1, wherein the terminal strip of the stationary connector member is mounted to a support plate or frame.

4. A connector as claimed in claim 2, further comprising means for removably securing the case of the movable connector member to the stationary connector member, which means are operable regardless of the electric connection condition between the terminal strip of the movable connector member and the terminal strip of the stationary connector member.

5. A connector as claimed in claim 1, wherein said wall is a wall of a case for the operating units of an ultrasound imaging apparatus or a wall integral with the framework of the stationary connector member and which is designed to close a coincident aperture of said wall of the case of the ultrasound imaging apparatus.

6. A connector as claimed in claim 5, wherein said terminal strip and the engagement frame of the stationary connector member are oriented transverse, particularly perpendicular to said front wall and the engagement frame is aligned with the slot in said front wall.

7. A connector as claimed in claim 1, further comprising means for removably mechanically locking each of the two movable connector members to the stationary connector member, which means removably hold the case of the two movable connector members against the framework or the front wall of the stationary connector member with the terminal strips of said movable connector members in their fully inserted position within the corresponding engagement frames.

8. A connector as claimed in claim 1, wherein said connector has more than two separate terminal strips in the same stationary connector member, each being associated with an engagement frame and being displaceable towards or away from such engagement frame using manual drive means.

9. A connector as claimed in claim 1, wherein the movable connector member is the terminal connecting a multi-pole cable of an ultrasound probe to an ultrasound imaging apparatus.

10. A connector as claimed in claim 9, wherein the stationary connector member is the terminal connecting the circuits of the ultrasound imaging apparatus to one or two ultrasound probes having the movable connector member.

11. A multi-pole connector comprising:
a first movable connector member with a plurality of first electric contact terminals supported by at least one terminal strip, said first electric contact terminals being defined by electrically insulated islands of material arranged in a predetermined layout or geometrical pattern, said movable member being designed to be mechanically and electrically coupled to a second stationary connector member which has at least one terminal strip with a plurality of second electric contact terminals thereon, in the form of electrically insulated islands of material arranged in the same said predetermined layout or geometrical pattern;
means for mechanically coupling the terminal strip of the movable connector member to the second connector member and means for mutual relative displacement of the terminal strip of the stationary connector member and the terminal strip of the movable connector member, in a position of coincidence, with reference to the direction of displacement, of the contact terminal patterns on both terminal strips into a state of adhesion of the contact terminals of one terminal strip to those of the other terminal strip, the direction of mechanical coupling of the terminal strip of the movable connector member being parallel to said strip and the direction of relative displacement of the terminal strip of the stationary connector member against the terminal strip of the movable connector member or vice versa being perpendicular to said terminal strip;
an engagement frame for the terminal strip of the movable connector member provided above the terminal strip of the stationary connector member, which frame is open on a receiving side, wherefore the terminal strip of the movable connector member is introduced into said engagement frame by a movement parallel to the surface of the terminal strip;
means for mutually centering the terminal strips of the stationary member and the movable member of the connector into a relative position in which each island of conductive material of the plurality of islands of conductive material on one of the terminal strips coincides with a corresponding island of conductive material of the plurality of said islands of conductive material on the other of said terminal strips;
wherein the terminal strip of the stationary connector member is supported in such a manner as to be able to move in a direction perpendicular to the frame that receives the terminal strip of the movable connector member, by the provision of manually driven displacement means; and
wherein said terminal strip of the stationary connector member having such a displacement stroke that said terminal strip is alternately displaced into a position in which it adheres against the terminal strip of the movable connector member within the engagement frame and a position in which the terminal strip of the stationary connector member is away from the terminal strip of the movable connector member within the engagement frame; and further comprising
mechanical displacement means for displacement of the terminal strip of the stationary connector member, which are manually driven and are designed to be driven for displacing said terminal strip away from the terminal strip of the movable connector member when the latter is within the engagement frame, against the action of an elastic means that stably push the terminal strip of the stationary connector member against the terminal strip of the movable connector member within the engagement frame, when the manually driven mechanical displacement means are in a disabled state, defined when the terminal strip of the stationary connector member is not displaced and held away from the engagement frame or the terminal strip of the movable connector member inserted in said engagement frame.

12. A connector as claimed in claim 11, wherein the movable connector member is the terminal connecting a multipole cable of an ultrasound probe to an ultrasound imaging apparatus.

13. A connector as claimed in claim 12, wherein the stationary connector member is the terminal connecting the circuits of the ultrasound imaging apparatus to one or two ultrasound probes having the movable connector member.

14. A multi-pole connector comprising:
a first movable connector member with a plurality of first electric contact terminals supported by at least one terminal strip, said first electric contact terminals being defined by electrically insulated islands of material arranged in a predetermined layout or geometrical pattern, said movable member being designed to be mechanically and electrically coupled to a second stationary connector member which has at least one terminal strip with a plurality of second electric contact terminals thereon, in the form of electrically insulated islands of material arranged in the same said predetermined layout or geometrical pattern;
means for mechanically coupling the terminal strip of the movable connector member to the second connector member and means for mutual relative displacement of the terminal strip of the stationary connector member and the terminal strip of the movable connector member, in a position of coincidence, with reference to the direction of displacement, of the contact terminal patterns on both terminal strips into a state of adhesion of the contact terminals of one terminal strip to those of the other terminal strip, the direction of mechanical coupling of the terminal strip of the movable connector member being parallel to said strip and the direction of relative displacement of the terminal strip of the stationary connector member against the terminal strip of the movable connector member or vice versa being perpendicular to said terminal strip;
an engagement frame for the terminal strip of the movable connector member provided above the terminal strip of the stationary connector member, which frame is open on a receiving side, wherefore the terminal strip of the movable connector member is introduced into said engagement frame by a movement parallel to the surface of the terminal strip;
means for mutually centering the terminal strips of the stationary member and the movable member of the connector into a relative position in which each island of conductive material of the plurality of islands of conductive material on one of the terminal strips coincides with a corresponding island of conductive material of the plurality of said islands of conductive material on the other of said terminal strips;
wherein the terminal strip of the stationary connector member is supported in such a manner as to be able to move in a direction perpendicular to the frame that receives the terminal strip of the movable connector member, by the provision of manually driven displacement means;

wherein said terminal strip of the stationary connector member having such a displacement stroke that said terminal strip is alternately displaced into a position in which it adheres against the terminal strip of the movable connector member within the engagement frame and a position in which the terminal strip of the stationary connector member is away from the terminal strip of the movable connector member within the engagement frame; and wherein the stationary connector member comprises a framework in which guides are provided for the displacement of the terminal strip of said stationary connector member, in a direction perpendicular to the front surface of said terminal strip and in a direction perpendicular to the engagement frame which is fixedly secured to said framework in a position parallel to the terminal strip and coincident therewith in a direction of displacement thereof, whereas said framework further has elastic pushing means for pushing the terminal strip, interposed between the side of the terminal strip away from the engagement frame and a stationary stop on said side of the terminal strip and whereas the framework supports a mechanism for pushing and translating the terminal strip in the direction away from the engagement frame while counteracting the pushing action of said elastic means, members being further provided for driving said mechanism, which are susceptible of being seized by one hand and operated with such hand.

15. A connector as claimed in claim 14, wherein the terminal strip of the movable connector member is fixed to a support plate or frame, the side edges oriented in the engagement direction of said support plate or frame being shaped complementary to the branches oriented in the engagement direction of the engagement frame, which act as guides for insertion of the terminal strip of the movable connector member and hold said terminal strip inserted in the engagement frame upon its translation perpendicular to the engagement direction.

16. A connector as claimed in claim 15, wherein the terminal strip of the stationary connector member is mounted, directly or via a support frame or plate, in such a manner as to slide or move parallel to itself along guides oriented perpendicular to the faces of the terminal strip, whereas the terminal strip and/or the support frame or plate are connected to a translation mechanism driven by a rocking control lever;

said translation mechanism including a rotating shaft mounted to the framework of the stationary connector member, which shaft is oriented perpendicular to the direction of insertion into the engagement frame and parallel to the faces of the terminal strip of the stationary connector member, and which shaft supports a cam lying on the side of the terminal strip facing towards the engagement frame and facing away from the side of said terminal strip against which the elastic pushing means operate, which cam is designed with such a shape that a predetermined rotation of the shaft moves the terminal strip directly and/or via the support frame or plate to a position away from the engagement frame and hence from a terminal strip possibly received in said engagement frame in a contact position of the terminal strip of the stationary connector member against a terminal strip of a movable connector member inserted in said engagement frame.

17. A connector as claimed in claim 16, wherein the terminal strip of the stationary connector member and the terminal strip of the movable connector member, or the engagement frame and/or the support plates or frames of the terminal strips on or in the corresponding connector member have complementary and cooperating centering means, which come into operation as the two terminal strips reach their mutual contact position.

18. A connector as claimed in claim 17, wherein one or both terminal strips and/or support frames and/or support plates and/or the engagement frame have centering teeth or ridges which project perpendicular to the opposed sides of said plates and/or frames and are aligned with engagement holes, with reference to the direction of said plates or strips and/or said frames towards each other, said centering teeth or ridges being formed into a shape that tapers towards the free end, and particularly into a conical or frustoconical shape.

19. A connector as claimed in claim 14, wherein the engagement frame is provided in combination with means for stopping the stroke of the terminal strip of the movable connector member into the engagement frame of the stationary connector member, which means are in such position as to ensure that the terminal strip of the movable connector member within the engagement frame and the terminal strip of the stationary connector member lie over each other with the contact terminals on said two terminal strips, in alignment with each other, with reference to the direction of displacement of said terminal strip of the stationary connector member.

20. A multi-pole connector comprising:
a first movable connector member with a plurality of first electric contact terminals supported by at least one terminal strip, said first electric contact terminals being defined by electrically insulated islands of material arranged in a predetermined layout or geometrical pattern, said movable member being designed to be mechanically and electrically coupled to a second stationary connector member which has at least one terminal strip with a plurality of second electric contact terminals thereon, in the form of electrically insulated islands of material arranged in the same said predetermined layout or geometrical pattern; and means for mechanically coupling the terminal strip of the movable connector member to the second connector member and means for mutual relative displacement of the terminal strip of the stationary connector member and the terminal strip of the movable connector member, in a position of coincidence, with reference to the direction of displacement, of the contact terminal patterns on both terminal strips into a state of adhesion of the contact terminals of one terminal strip to those of the other terminal strip, the direction of mechanical coupling of the terminal strip of the movable connector member being parallel to said strip and the direction of relative displacement of the terminal strip of the stationary connector member against the terminal strip of the movable connector member or vice versa being perpendicular to said terminal strip;

wherein said at least one terminal strip comprises two terminal strips, each underlying an engagement frame for the terminal strip of the movable connector member, the terminal strip-engagement frame pairs laying one above the other and each engagement frame being stationary, whereas the two terminal strips are stressed towards the associated engagement frames by elastic means and are designed to be moved away from said engagement frame by manually driven mechanical displacement means so that each terminal strip is alternately brought into a position of contact with a terminal strip of a movable connector member within the associated engagement frame and into a position spaced from said terminal strip of the movable connector member within the associated engagement frame.

21. A connector as claimed in claim 20, wherein the terminal strips are mounted in such an arrangement as to be able to slide along guides directly or via a support frame or a support plate, to, in or on which each terminal strip is fixed, whereas a separate mechanism for manually driving the displacement of the terminal strip is provided for each terminal strip and/or for each corresponding support frame or each corresponding support plate.

22. A connector as claimed in claim 21, wherein the means for displacement of the two terminal strips of the stationary connector member are a common shaft and a common rotary drive member for said shaft, which controls separate pushing members, each cooperating with a stop member for one of the two terminal strips or the corresponding support frame or the corresponding support plate.

23. A connector as claimed in claim 22, wherein said pushing means includes a separate cam for each terminal strip.

24. A connector as claimed in claim 20, wherein, since an ultrasound imaging system operates with one probe at a time, the displacement means are driven by common drive means and in a synchronized manner, such that in a first drive state of the drive means one of the two terminal strips of the stationary connector member is brought into contact with the terminal strip of a movable connector member within the corresponding engagement frame whereas the second terminal strip is brought away from the corresponding engagement frame or the terminal strip of a movable connector member within the engagement frame; and in a second alternative drive state, the first of the terminal strips of the stationary connector member is away from a terminal strip of a movable connector member within the engagement frame cooperating with said terminal strip of the stationary connector member, whereas the second terminal strip of the stationary connector member is in contact with a terminal strip of a movable connector member within said engagement frame;

and in a third alternative drive state, both terminal strips are moved away from their respective engagement frames or from a terminal strip of two movable connector members, each of which terminal strips is within one of the two engagement frames.

25. A connector as claimed in claim 24, wherein the displacement means are comprised of two cams each cooperating with one of the two terminal strips of the stationary connector member, said two cams being rotatably driven by a common drive shaft and the two cams being shaped and placed in such angular positions relative to each other to move either both terminal strips away from their respective engagement frames or one of said two cams away from its engagement frame and the other to contact with a terminal strip of a movable connector member within the corresponding engagement frame.

* * * * *